(12) United States Patent
Dreyer et al.

(10) Patent No.: US 7,132,118 B2
(45) Date of Patent: Nov. 7, 2006

(54) CUCUMIS MELO EXTRACT COATED AND/OR MICROENCAPSULATED IN A FAT-SOLUBLE AGENT BASED ON A FATTY SUBSTANCE

(75) Inventors: Alain Dreyer, Chateauneuf de Gadagne (FR); Jean-Paul Ginoux, Eyragues (FR); Philippe Roch, Eyragues (FR); Dominique Lacan, Montpellier (FR); Christian Yard, Combas (FR)

(73) Assignee: Bio-Obtention SC, Montferrier-sur-lez (FR)

( * ) Notice: Subject to any disclaimer, the term of this patent is extended or adjusted under 35 U.S.C. 154(b) by 499 days.

(21) Appl. No.: 10/446,672

(22) Filed: May 29, 2003

(65) Prior Publication Data

US 2003/0203052 A1 Oct. 30, 2003

Related U.S. Application Data

(62) Division of application No. 09/850,037, filed on May 8, 2001, now abandoned.

(30) Foreign Application Priority Data

Mar. 20, 2001 (FR) .................... 01 03750

(51) Int. Cl.
*A61K 36/00* (2006.01)
*A61K 9/16* (2006.01)
*A61K 38/43* (2006.01)

(52) U.S. Cl. .............. 424/725; 424/490; 424/94.1
(58) Field of Classification Search .............. None
See application file for complete search history.

(56) References Cited

U.S. PATENT DOCUMENTS 4,273,790 A * 6/1981 Bosco et al. ............. 426/335
4,788,072 A * 11/1988 Kawamura ............... 426/441
5,061,496 A * 10/1991 Cherukuri et al. ............ 426/3
5,616,323 A * 4/1997 Ginoux et al. ............ 424/758
5,747,043 A * 5/1998 Ginoux et al. ............ 424/758
6,238,672 B1 * 5/2001 Chen ....................... 424/728
6,342,208 B1 * 1/2002 Hyldgaard et al. .......... 424/59
6,720,014 B1 * 4/2004 Short et al. ................ 426/52

FOREIGN PATENT DOCUMENTS

| FR | 2 225 443 | 11/1974 |
|----|-----------|---------|
| FR | 2 240 277 | 3/1975 |
| FR | 2 287 899 | 5/1976 |
| FR | 2 716 884 | 9/1995 |
| FR | 2 729 296 | 7/1996 |
| WO | 92/02622 | 2/1992 |

OTHER PUBLICATIONS

Keele, Jr. et al.; Superoxide Dismutase from *Escherichia coli* B The Journal of Biological Chemistry, vol. 245, No. 22, 1970; pp. 6176-6181.

Markowitz et al.; Studies on copper Metabolism, XXVII. The Isolation and Properties of an Erythrocyte Cuproprotein (Erythrocuprein) ; J. Biol. Chem., 234, 1959, pp. 40-45.

Delanian et al.; Successful treatment of radiation-induced fibrosis using liposomal Cu/Zn superoxide dismutase: clinical trial; Radiotherapy & Oncology 32 (1994) pp. 12-20.

Emerit et al.; Phase II Trial of Copper Zinc Superoxide Dismutase (CuZn SOD) in the Treatment of Crohn's Disease; Free Rad. Res. Comms., vols. 12-13, pp. 563-569, 1991.

* cited by examiner

*Primary Examiner*—Christopher R. Tate
(74) *Attorney, Agent, or Firm*—Jacobson Holman PLLC (57) ABSTRACT

The present invention relates to a composition comprising an active plant extract containing superoxide dismutase, said extract being coated and/or microencapsulated in a fat-soluble agent based on a fatty substance.

It also relates to its method of manufacture, to the pharmaceutical, cosmetic or food compositions containing it and as a medicament, in particular, in protecting the epidermis against UV radiation and allergies.

7 Claims, 5 Drawing Sheets

CUCUMIS MELO EXTRACT COATED AND/OR MICROENCAPSULATED IN A FAT-SOLUBLE AGENT BASED ON A FATTY SUBSTANCE

This is a divisional of application Ser. No. 09/850,037 filed May 8, 2001 now abandoned.

The present invention relates to a novel composition comprising an active plant extract containing superoxide dismutase, in particular a protein extract of *cucumis melo*. It relates in particular to active plant extracts coated and/or microencapsulated in a fat-soluble agent based on a fatty substance and which may be useful in oral or topical application.

While oxygen is essential for us to function, it nevertheless generates toxic reactive oxygen species which have a negative effect on our body.

In biological systems, reactive oxygen species comprise free radicals such as the superoxide radical ($O_2.^-$), the hydroxyl radical (OH.), nitrogen monoxide (NO.) or peroxyl radicals of lipid origin (L-OO.). These free radicals are atoms or molecules whose electron configuration is characterized by the presence of an unpaired electron. This characteristic feature makes them unstable and, to become stabilized, they can rapidly oxidize new biological molecules such as nucleic acids (DNA), enzymatic proteins or membrane lipids and particularly polyunsaturated fatty acids (PUFA). The superoxide ion is the free radical most commonly and most abundantly generated in cells. It therefore represents a considerable danger for the body. Its toxicity depends in particular on its transformation to other more aggressive reagents such as the hydroxyl radical (OH.).

Our body acts constantly against the formation of free radicals and several lines of defense may be envisaged for detoxifying the cell.

The first line of defense is provided by an enzyme called superoxide dismutase (SOD). Three forms of SOD exist: one containing copper and zinc, ie. Cu/Zn SOD; another containing manganese (Mn SOD) and finally one SOD containing iron (Fe SOD°). SOD plays a key role in combating free radicals since it allows the elimination of the superoxide ion. Superoxide dismutases are enzymes capable of inducing dismutation of the superoxide ions according to the reaction:

$$2O_2 + 2H^+ \rightarrow H_2O_2 + O_2$$

This elimination of the superoxide ion leads nevertheless to the formation of hydrogen peroxide ($H_2O_2$) which is also toxic for the cell. The action of SOD should therefore be supplemented by a second line of defense which eliminates $H_2O_2$.

The second line of defense is provided by two enzymes: catalase and selenium-dependent glutathione peroxidase (SeGPx) which destroys $H_2O_2$.

Under normal biological conditions, the human body constantly produces, but in low quantities, free radicals which are immediately neutralized by the existing defense systems. In some cases, if the production of free radicals increases (tobacco, stress, pollution, solar radiation and the like) and/or if there is a deficiency in antioxidant substances, this leads to an oxidant/antioxidant imbalance. This imbalance is increasingly closely correlated with numerous pathological conditions and with numerous imbalances. Because of this, the search for antioxidant substances has been a subject of constant interest in the sector of cosmetology, agro-foodstuffs or medicine.

Patent FR 2 287 899 has described, for example, the application in cosmetology of superoxide dismutase enzymes and in particular the use of these enzymes in the preparation of cosmetic compositions for skin and hair care.

SOD has therefore been used in pathological conditions induced by free radicals, in particular in the case of chronic inflammations such as, for example, in the treatment of Crohn's disease (Emerit et al., 1991, *Free Rad. Res. Comms*, 12–13, 563–569) or in the case of radio-induced fibroses (Delanian et al., 1994, *Radiotherapy and Oncology*, 32, 12–20).

These superoxide dismutases are in particular extracted from bovine erythrocytes (Markovitz, *J. Biol. Chem.*, 234, p. 40, 1959), from *Escherichia Coli* (Keele and Fridovitch, *J. Biol.*, 245, p. 6176, 1970) and from marine bacterial strains (patents FR 2 225 443 and FR 2 240 277).

Nevertheless, for reasons linked in particular to the infectious substances which these materials may contain, there is currently a tendency to replace them with substances obtained from the plant kingdom which are reputed to be more healthy. These antioxidant enzymes are indeed present in variable quantities in some plants.

Thus, patent application FR 2 716 884 describes a protein extract of *Cucumis melo* having improved superoxide dismutase enzymatic activity, their method of preparation and their use in pharmaceutical or cosmetic compositions for external topical use. However, such a protein extract is difficult to use as the enzymes which it contains (superoxide dismutase in particular) are inactivated in the presence of external attacks (UV in particular) or while taking in formulations for oral use (gastric juice). It is therefore advisable to develop specific formulations which offer this protection so as to optimize the action of the antioxidant active agents.

To increase the plasma half-life of the free forms of SOD (Cu/Zn, Fe or Mn), various modified forms for parenteral administration have been proposed; there may be mentioned SODs conjugated with polyethylene glycol (SOD-PEG), SODs conjugated with heparin (SOD-Heparin), SODs conjugated with albumin (SOD-albumin), polymers or copolymers of SOD and liposomal SODs. However, these various SODs have the major disadvantage of being only very slightly absorbed when they are administered by the oral route.

Patent application FR 2 729 296 also describes a particular pharmaceutical composition which is well suited to oral administration of superoxide dismutase essentially comprising, in combination, a superoxide dismutase and a compound selected from the group consisting of ceramides, prolamines and polymeric films based on said prolamines. However, such a composition is not suitable for use by the topical route and, in addition, cannot be used by people allergic to gluten.

The inventors have discovered, surprisingly, that when an active plant extract containing superoxide dismutase (SOD) was coated and/or microencapsulated in a fat-soluble agent based on a fatty substance, it could be used by the topical or oral route and its active agents, in particular SOD, were protected against external attacks (UV or gastric juice for example).

The present invention therefore relates to a composition comprising an active plant extract containing superoxide dismutase, said extract being coated and/or microencapsulated in a fat-soluble agent based on a fatty substance.

The expression "active plant extract containing superoxide dismutase" is understood to mean, for the purposes of the present invention, any extract obtained from plants having superoxide dismutase enzymatic activity. Advantageously, it is a protein extract of *cucumis melo*, in particular in powdered form, advantageously freeze-dried. More advantageously still, the *cucumis melo* is a progeny of the cell line 95LS444, whose seeds have been deposited in accordance with the Budapest Treaty in the NCIMB Collection (National Collection of Industrial and Marine Bacteria-ABERDEEN AB2 1RY (Scotland-GB) 23 St. MacharDrive) on Jul. 19, 1990 under the No. 40310, or of one of the hybrid lines derived from 95LS444.

In a particular embodiment, the superoxide dismutase enzymatic activity of the plant extract is at least equal to 5 enzymatic units per mg of extract, advantageously at least equal to 50 enzymatic units per mg of extract.

The plant extract may be obtained by methods well known to persons skilled in the art, in particular by the method described in patent application FR 2 716 884. It is also commercially available from the company BIONOV under the trademark EXTRAMEL®.

Advantageously, the plant extract according to the present invention may, in addition, have a catalase enzymatic activity. It may also comprise a coenzyme Q10, vitamins, lipoic acid, gluthathione, inorganic elements present in the plant, such as potassium, magnesium, calcium and selenium, and the like.

The expression "fat-soluble agent based on a fatty substance" is understood to mean, for the purposes of the present invention, any agent containing at least one fatty substance and having an index of balance between the hydrophilic part and the lipophilic part of the molecule (HLB) of less than 10.

Advantageously, the fat-soluble agent according to the present invention has a melting point of between about 40 and about 80° C., more advantageously still of between about 55 and about 60° C.

In a particular embodiment, the fat-soluble agent according to the present invention is of plant origin. Advantageously, it is chosen from the group consisting of hydrogenated oils; palm oil or oil from the heart of palm fruit; hydrogenated seeds; stearates, in particular chosen from stearins, stearic acid and its derivatives; waxes; fatty acid monodiglycerides; saturated $C_{14}$–$C_{20}$ fatty acid triglycerides and mixtures thereof.

Advantageously, the fat-soluble agent according to the present invention is hydrogenated oil based on plant oil, in particular chosen from the group consisting of hydrogenated coconut oil, hydrogenated palm oil, hydrogenated soybean oil or hydrogenated rapeseed oil and mixtures thereof. More advantageously still, it is hydrogenated palm oil.

It is also possible for the fat-soluble agent to contain water-soluble substances of the sugar or polyol type.

In a particular embodiment, the plant extract according to the invention is present at a concentration of between 1 and 90% by weight relative to the total weight of the composition, advantageously between 20 and 50% by weight relative to the total weight of the composition.

The present invention also relates to a method for manufacturing the compositions according to the present invention comprising the following steps:
 a) melting the fat-soluble agent,
 b) depositing the liquid obtained in step a) on the active plant extract containing superoxide dismutase.

Advantageously, the plant extract is present of the form of a powder and step b) is carried out in a fluidized bed, more advantageously still at low temperature and a low moisture content.

In a particular embodiment, the temperature of step b) is less than the melting point of the fat-soluble agent and is advantageously about 40° C.

The present invention also relates to a pharmaceutical or cosmetic composition comprising a composition according to the invention and an excipient appropriate for oral or topical use for human or animal administration. These compositions may be formulated for administration to mammals, including humans. The dosage varies according to the treatment and according to the condition in question.

In a particular embodiment, the pharmaceutical or cosmetic composition according to the present invention may be formulated for administration by the oral route. The active ingredient may be administered in unit forms for administration, mixed with conventional pharmaceutical carriers, to animals or to human beings. The appropriate unit forms for administration comprise the forms such as tablets, gelatin capsules, powders, granules and oral solutions or suspensions. Advantageously, it comprises, in addition, yogurt and/or fibers, more advantageously still so as to form a homogeneous mixture with the composition comprising an active plant extract containing superoxide dismutase, said extract being coated and/or microencapsulated in a fat-soluble agent based on a fatty substance according to the present invention.

In another particular embodiment of the invention, the pharmaceutical or cosmetic composition may also be formulated for administration by the topical route. They may be provided in the forms which are customarily known for this type of administration, that is to say in particular lotions, foams, gels, dispersions, sprays, shampoos, serums, masks, body milks or creams for example, with excipients allowing in particular skin penetration so as to improve the properties and the accessibility of the active ingredient. These compositions generally contain, in addition to the composition according to the present invention, a physiologically acceptable medium, in general based on water or solvent, for example alcohols, ethers or glycols. They may also contain surfactants, preservatives, stabilizing agents, emulsifiers, thickeners, other active ingredients leading to an additional or potentially synergistic effect, trace elements, essential oils, perfumes, colorants, collagen, chemical, or mineral filters, moisturizing agents or thermal waters.

The present invention also relates to a composition according to the present invention as a medicament.

Advantageously, it relates to a composition according to the present invention as a medicament intended for treating or for preventing allergies or for protection the epidermis from UV radiation.

The present invention also relates to the use of a composition according to the present invention for the manufacture of a medicament for topical use intended for treating allergies, eczema, vitiligo, psoriasis, lupus, skin fibrosis, for eliminating melanomas, for improving cicatrizations of transplants, for preventing allergies or for protecting the epidermis from UV radiation.

It also relates to the use of a composition according to the present invention for the manufacture of a medicament intended for protecting the epidermis from UV radiation, for treating or preventing allergies, for treating asthma, anemia, male sterility, inflammatory diseases such as anthropathy or degenerative diseases due to cellular and/or Organic degeneration, in particular chosen from the group consisting of Crohn's disease, Parkinson's disease, Alzheimer's disease, colorectal cancers, fibroses of varied origins, degenerations due to an infectious agent such as AIDS or hepatitis C or degenerations linked to the use of a medicament.

The present invention also relates to the use of a food composition comprising the composition according to the present invention as an energy source, as a tonic source or as an aid for recuperation and for regaining fitness.

It relates, furthermore, to a composition according to the present invention as a medicament, in particular for topical use, intended for treating or for preventing allergies, advantageously for protecting the epidermis against allergies.

It finally relates to the use of a composition according to the present invention for the manufacture of a medicament, in particular for topical use, intended for treating or for preventing allergies, advantageously for protecting the epidermis against allergies.

BRIEF DESCRIPTION OF THE DRAWINGS

Other objects and advantages of the invention will become apparent for persons skilled in the art through references to the following illustrative drawings.

The following examples are given as a guide, without limitation.

EXAMPLE 1

Preparation of a Composition According to the Present Invention

Preparation of an Active Plant Extract (Described in Patent Application FR2 716 884)

5 g of pulp from a hybrid *cucumis melo* derived from the cell line 95LS444 (described in international application WO 92/02622) are ground in a mortar in the cold state. A volume of 50 mM phosphate buffer (pH: 7.5; 5EDTA 1 mM; glycerol 5%) equivalent to 3 times the plant mass is added. After homogenization, the suspension is centrifuged at 5000 g at 4° C. for 30 minutes. The supernatant is then recovered and filtered. This crude extract serves for the determination of the superoxide dismutase activity. It is measured with the aid of an SOD 525 assay kit provided by the company Bioxytech. This method gives results comparable to those obtained by the McCord and Fridovitch method (inhibition by SOD of the reduction of cytochrome C by xanthine-xanthine oxidase).

Preparation of the Composition According to the Present Invention

The active plant extract prepared above in the form of a freeze-dried powder which is also sold by the company BIONOV under the trademark EXTRAMEL® is used. This extract, after coating, has an SOD activity of 14 units per mg of extract and also contains catalase and coenzyme Q10.

The fat-soluble agent used is hydrogenated palm oil.

Figure 1:
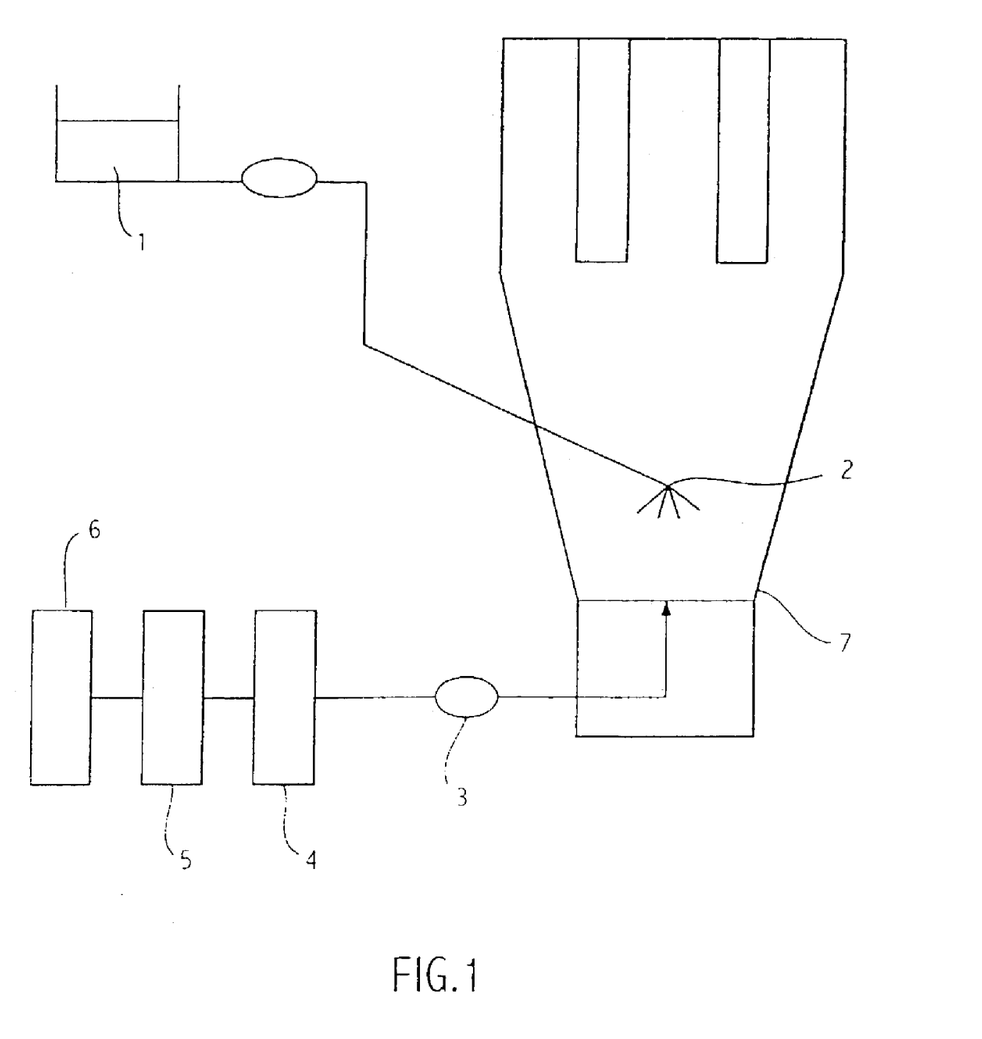
FIG. 1 represents a skeleton diagram of the process for the preparation of the compositions according to the present invention.

The melting of this agent is carried out in the container (1) (FIG. 1) by heating. The liquid agent thus obtained is deposited by spraying with the aid of a bifluid Schlick nozzle (2) onto the powder of the active plant extract suspended in a fluidized bed (7) at low temperature ("skin" temperature less than 40° C.) and a low moisture content. The low melting point of this coating agent (58 to 61° C.) allows instant solidification of the material without burning the active plant extract. According to FIG. 1, a ventilator (3), a heater (4), a desaturation device (5) and a filter (6) are used.

The composition thus obtained contains 20% by weight of the active plant extract and 80% by weight of the fat-soluble agent.

EXAMPLE 2

Production of a Semisolid Preparation for Local Application Comprising a Composition According to the Present Invention The preparation (oil-in-water emulsion) is produced in a manner well known to persons skilled in the art using the ingredients and the proportions indicated in Table 1.

TABLE 1

Ingredients and proportions for the semisolid preparation

| INGREDIENTS | % by weight |
| --- | --- |
| Refined macadamia oil (Soetenaey Laboratoire, Fécamp) | 33% |
| Kosteran—S/1 G (Verfilco-Fontenay S/Bois) | 3.8% |
| Kotilen—S/1 (Verfilco-Fontenay S/Bois) | 1.2% |
| Water | QS 100% |
| Composition according to Example 1 | 2.2% |
| Preservative (Sepicide; Seppic; Castres) | 0.3% |

A semisolid preparation for local application is obtained which has the characteristics indicated in the following Table 2.

TABLE 2

Characteristics of the semisolid preparation
for local application according to Example 2

| Appearance | Fine emulsion |
|---|---|
| pH | 6.93 |
| Stability | Stable at room temperature |
|  | Stable at 40° C. |
|  | Stable in heat cycle |

EXAMPLE 3

Evaluation of the Protective Activity of the Composition According to Example 1 in Relation to UV Radiation In Vitro on Normal Human Keratinocytes The object of this study is to evaluate the protective effect of the composition according to Example 1 in relation to UV radiation which has as principle consequences in the epidermis the induction of premature death of the keratinocytes by apoptosis (Sun Burn Cell) as well as a release of soluble mediators which contribute to the development of a local inflammation.

Among these proinflammatory mediators whose production appears to be stimulated by UV radiation, even at very low doses, there may be mentioned IL-1α, TNF-α, IL-6 and the free radical NO. The latter is in fact produced by the oxidative conversion of arginine to citrulline in the presence of oxygen via inducible NO-Synthase which is expressed following UV stress. A major proinflammatory mediator, NO appears to be the main agent responsible for tissue degradations linked to the inflammatory state.

The protective effect of the active plant extract sold by the company BIONOV under the trademark EXTRAMEL® and of the composition according to Example 1 was evaluated in an experimental approach based on an in vitro model which makes it possible to determine cellular apoptosis as well as the production of proinflammatory mediators following UV irradiation.

In this study, it was chosen to study, in a first instance, the production of the proinflammatory cytokines TNF-α and IL-6 and of the NO radical by keratinocytes subjected to UVB radiation.

a) Material and Methods

Cells

The keratinocytes are obtained from primary cultures of foreskins and are allowed to proliferate in a conditioned medium (Keratinocyte Growth Medium (KGM)) for two weeks before use. At confluence, the pure keratinocytes are cultured in 24-well plates at $10^6$ cells/ml in a medium free of growth factors in the presence or in the absence of the product to be tested for 24 h and are then stimulated by UV radiation.

Medium for Evaluating the Effects of the Product

During the evaluation of the product, the cells are cultured in Iscove medium supplemented with antibiotics (100 SOD units (U)/ml of penicillin and 100 µg/ml of streptomycin) and fetal calf serum (5%), and they are brought into contact with the composition according to Example 1 at various concentrations (0.1 to 1000 µg/ml) and then stimulated by UV radiation.

UV Stimulation:

The cells were irradiated with "¼ m Oriel Monochromator, 1 KW mercury-xenon arc lamp with a pass band of 5 nm and focused through a luminous liquid guide (5 nm×1 m). The irradiation is carried out at 14.4 Kj/m² at 310 nm for a period of 10 min, this type of irradiation corresponding to a UVB-type irradiation.

The determination of the production of the proinflammatory mediators TNF-α, IL-6 and NO is carried out 48 h after irradiation.

The percentage of apoptotic cells is evaluated 72 h after irradiation.

Measurement of Apoptosis

At the end of the culture, death by apoptosis is evaluated using the Apoptag® kit, the DNA breaks being visualized by fluorescence emission.

The number of cells undergoing apoptosis is evaluated by counting the number of fluorescent cells out of a total of 200 cells.

Assay of the Inflammation Mediators IL6, TN-α and NO

The assays of the cytokines TNF-α and IL-6 are carried out on culture supernatants using ELISA assay kits, the detection thresholds being each time less than 10 pg/ml. As regards the production of NO, it is in fact the stable derivatives, i.e. the nitrites, which are measured by a colorimetric technique using the Griess reagent.

b) Results

Apoptosis

The keratinocytic apoptosis appears to be greatly increased 72 h after UV irradiation as indicated in the following Table 3.

TABLE 3

Keratinocytic apoptosis induced by UV irradiation

| Treatment | % apoptosis relative to the total number of cells in culture |
|---|---|
| Keratinocytes (control) | 5 ± 2 |
| Keratinocytes/UV | 78 ± 4 |

These results therefore make it possible to institute this model as a model for evaluating products having a "protective" activity profile.

Influence of the Concentration of the Composition According to Example 1 on the Antiapoptotic Power The composition according to Example 1, tested in a concentration range of between 1 and 30 SOD units, is added 24 h before irradiation. Each experiment is carried out in triplicate.

Figure 2:
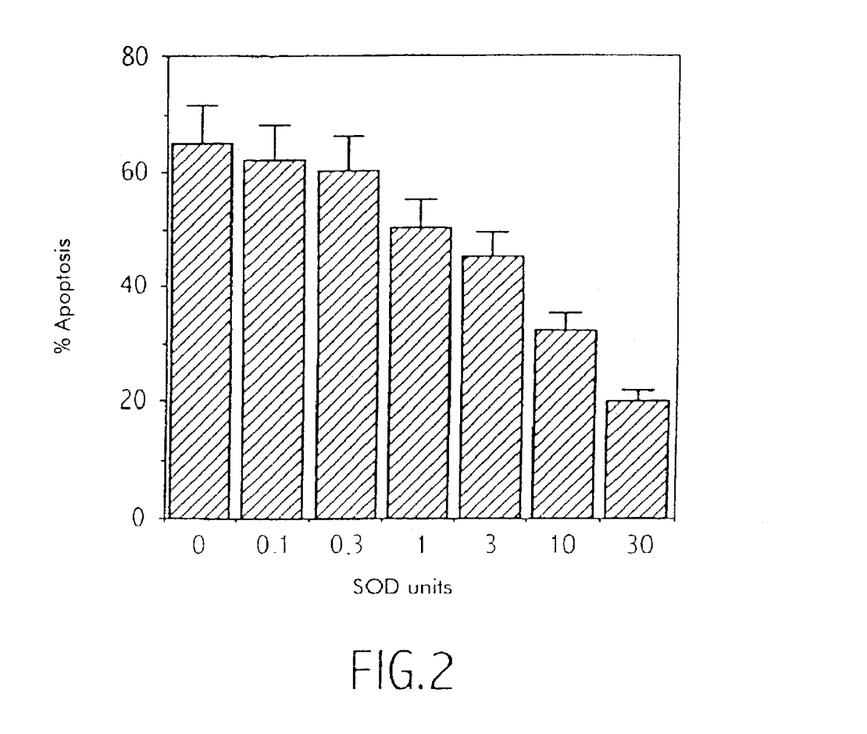
FIG. 2 represents the effects evaluated 72 hours after irradiation of the composition of the present invention administered 24 hours before irradiation on keratinocytic apoptosis induced by UV radiation as a function of its SOD concentration.

These effects are evaluated 72 h after irradiation and the % of cells undergoing apoptosis is evaluated by fluorescence microscopy after using the Apoptag® kit (FIG. 2).

These experiments clearly demonstrate that the composition according to the invention has a protective activity against the phenomenon of induction of apoptosis post-UV irradiation, when it is added preventively, that is to say before the irradiation phenomenon. During these experiments, the use of the active plant extract Extramel® at a dose of 30 SOD units produces an effect equivalent to 0.3 SOD units of the composition according to Example 1 which suggests that the active plant extract, when it is delivered intracellularly by the use of the protection in the form of a coating with the aid of a fat-soluble agent according to the present invention, is 100 times more effective than the free active plant extract.

Figure 3:
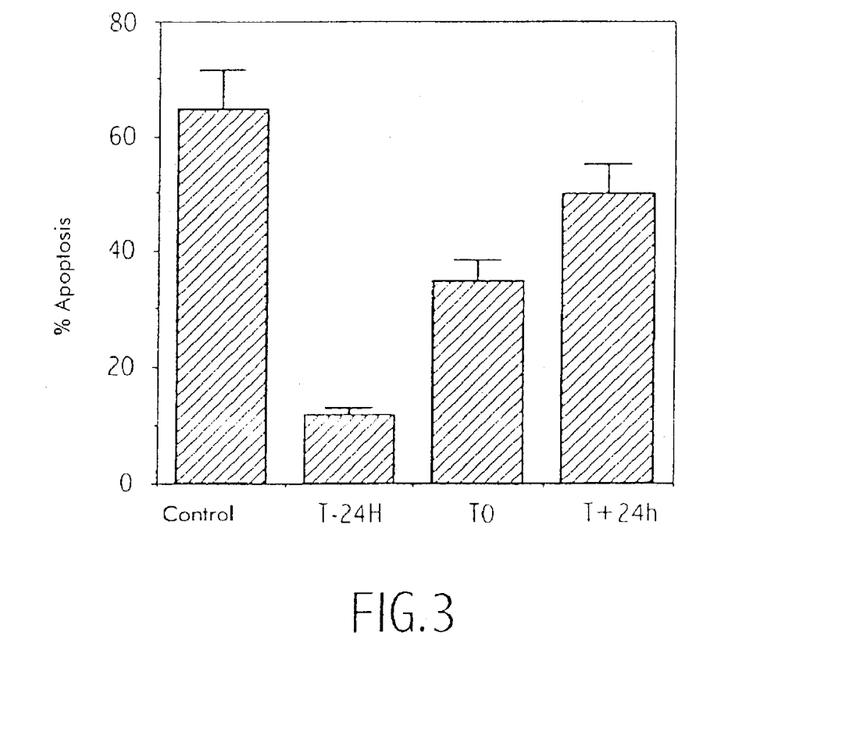
FIG. 3 represents the effects evaluated 72 hours after irradiation of the composition according to the present invention containing 30 units per ml of SOD on keratinocytic apoptosis induced by UV radiation as a function of its time of administration.

Influence of the Conditions for Adding the Composition According to Example 1 to the Culture Medium The concentration of the composition according to Example 1 selected for this study is 30 SOD units/ml (FIG. 3).

To determine the capacity of this composition to act on apoptosis induced by UV, preventively, immediately and post-irradiation, it was added 24 h before irradiation, at the beginning of irradiation and finally 24 h after irradiation, respectively.

Under the conditions of the study, a marked reduction in apoptosis is observed when the composition is added 24 h before irradiation (T−24 H).

Added at the beginning of irradiation (T0), the antiapoptotic effect of the composition according to Example 1 appears to be reduced and this effect is even more reduced when this composition is added 24 h after irradiation (T+24 H).

The product therefore appears to be very effective preventively.

Production of Cytokines and of NO

The stimulation of human keratinocytes by UV radiation (Table 4) under the conditions used for these experiments induces the production of the cytokines TNF-α and IL-6 and the production of NO, via the activation of inducible NO-Synthase in these cells.

Influence of the Conditions for Adding the Composition According to Example 1 to the Culture Medium on the Production of the Proinflammatory Mediators The capacity of the composition according to the present invention to modulate the production of proinflammatory mediators was evaluated according to the following experimental conditions: introduction of the composition according to Example 1 24 h before irradiation or at the beginning of irradiation or 24 h after irradiation.

The composition according to Example 1 is tested at 30 SOD units/ml. The assay of the mediators was carried out in triplicate. The results are presented in Table 4.

TABLE 4

Assay of the proinflammatory mediators 48 h after UV irradiation

| Treatment | TNF (pg/ml) | IL-6 (pg/ml) | $NO_2^-$ (µM) |
|---|---|---|---|
| None or the composition of Example 1 alone | Not detectable in the 3 experiments | Not detectable in the 3 experiments | 0.65 ± 0.25 |
| UV | 310 ± 75 | 255 ± 30 | 10 ± 2 |
| UV + composition according to Example 1 administered at T − 24 h | 95 ± 12 | 100 ± 18 | 1.5 ± 2 |
| UV + composition according to Example 1 administered at T0 | 125 ± 6 | 108 ± 4 | 6.5 ± 2 |
| UV + composition according to Example 1 administered at T + 24 h | 306 ± 17 | 212 ± 8 | 9.2 ± 2 |

A reduction in the production of the proinflammatory cytokines and in the nitro derivatives is observed when the composition according to Example 1 (30 U/ml) is added preventively (T−24 h) whereas this effect is reduced when the addition is made immediately (T0) and has little effect when the product is added 24 h after UV stimulation (T+24 h).

c) Conclusion

The production of the proinflammatory mediators as well as the death of the cells by apoptosis are phenomena linked to a massive production of free oxygen radicals (ROS) derived from an interaction between UV radiation and oxygen $O_2$. These free radicals are responsible for the oxidative stress generated by UV radiation.

When the physiological antioxidant pool is no longer able to control them, phenomena of cell degeneration accompanied by an inflammatory reaction develop.

The composition according to the present invention added before the UV stress inhibits the expression of the proinflammatory mediators and simultaneously reduces the entry of the cells into apoptosis.

In this study, it therefore clearly appears that the composition according to the present invention exerts a protective effect on the cellular metabolism.

Indeed, in the presence of the composition according to the present invention, the keratinocytic apoptosis induced by UV irradiation appears to be significantly reduced. Likewise, the increase in the production of proinflammatory mediators induced by UV irradiation, appears to be greatly attenuated (TNF-α, IL-6 and NO).

Consequently, the composition according to the present invention protects the skin tissue from the degeneration phenomena generated by oxidative stress, regardless of the origin thereof, whether physical (UV radiation) or chemical (environmental pollutants such as ozone, carbon monoxide or heavy metals, and the like), in particular when it is administered preventively.

In Vivo on Transplants of Human Skin onto "Nude" Mice

The object of this study is to evaluate the effect, by the oral route, of an active plant extract alone (Extramel®) or coated with a composition according to the present invention containing SOD against inflammation induced in the skin by UV radiation whose main consequence in the epidermis is to induce a release of soluble mediators which contribute to the development of a local inflammation.

Among these proinflammatory mediators, whose production appears to be stimulated by UV radiation, even at very low doses, there may be mentioned TNF-α and the free radical NO. The latter is in fact produced by the oxidative conversion of arginine to citrulline in the presence of oxygen via inducible NO-Synthase which is expressed following UV stress. A major proinflammatory mediator, NO appears to be the main agent responsible for tissue degradations linked to the inflammatory state.

The protective effect of the composition according to Example 1 (mixed or otherwise with food fibers and/or yogurt) was evaluated in an experimental approach based on the following model:

in vivo on explants of normal human skin which are transplanted onto nude mice and irradiated with UVB, only the portion of human skin being taken into account in the irradiation and in the evaluation of efficacy produced.

a) Materials and Methods

UV Stimulation

Mice carrying human skin were irradiated with "¼ m Oriel Monochromator, 1 KW mercury-xenon arc lamp with a pass band of 5 nm and focused through a luminous liquid guide (5 nm×1 m). The irradiation is carried out at 14.4 $Kj/m^2$ at 310 nm for a period of 10 min, this type of irradiation corresponding to a UVB-type irradiation.

The determination of the production of the proinflammatory mediators TNF-α and NO is carried out 48 h after irradiation on the skin explants.

Assay of the Inflammation Mediators TNF-α and NO

The assay of the cytokines TNF-α is carried out on culture supernatants using ELISA assay kits, the detection thresholds being each time less than 10 pg/ml. As regards the production of NO, it is in fact the stable derivatives, i.e. the nitrites, which are measured by a colorimetric technique using the Griess reagent.

b) Preliminary Results in Vivo

Figure 4:
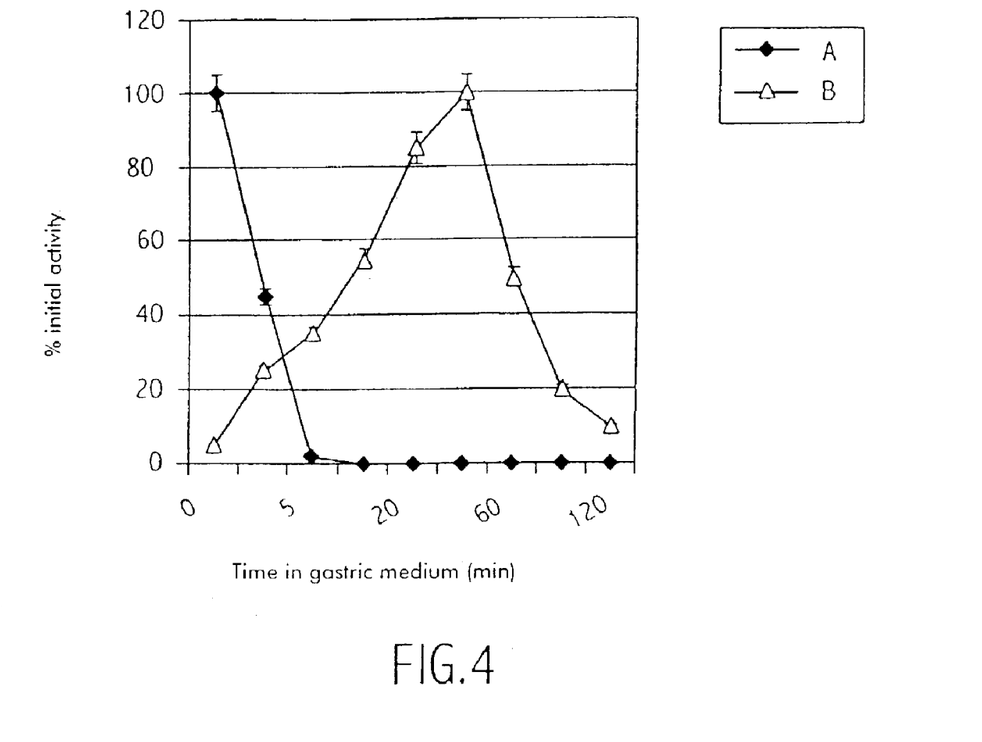
FIG. 4 represents the degradation time in gastric medium of the composition according to the present invention (B) compared with the uncoated active plant extract (A).
Figure 5:
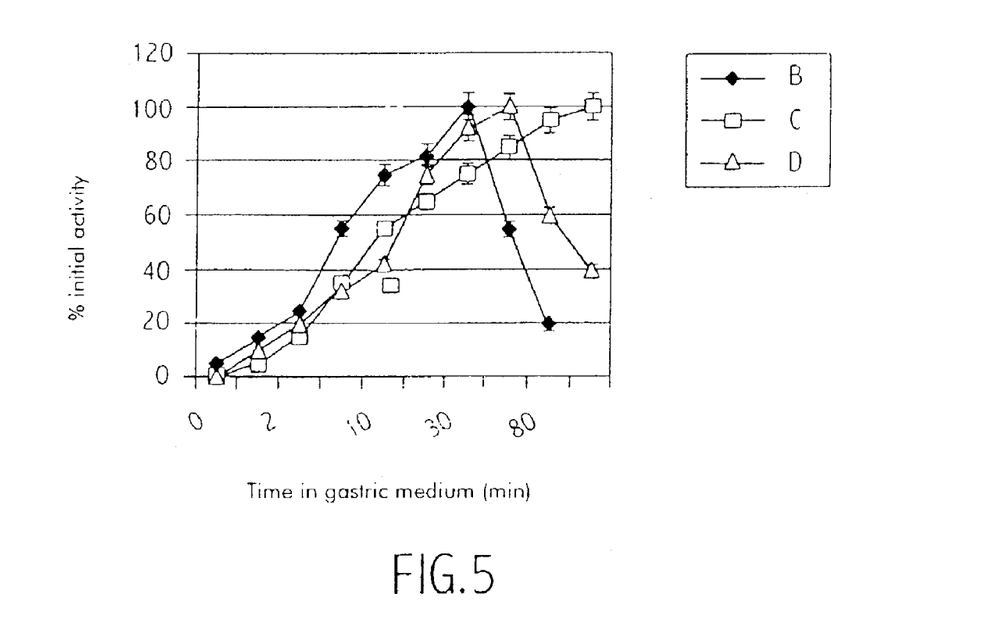
FIG. 5 represents the degradation time in gastric medium of the composition according to the present invention (B) compared with the composition according to the present invention homogeneously mixed with fibers (C) or yogurt (D).

A comparison was made (FIG. 4) between the degradation of the active plant extract marketed by the company BIONOV under the trademark EXTRAMEL® (A) and the composition according to Example 1 (B) (that is to say the same active plant extract, but this time protected by means of its coating with a fat-soluble agent). If the active plant extract is degraded in the minutes following its introduction into a medium mimicking the gastric juice (pH 1, trypsin and pepstatin), the composition according to Example 1 has an increased resistance. Indeed, this composition releases SOD progressively between 5 and 30 min (FIG. 4). However, while this composition does not exhibit absolute protection with respect to the digestive process, it appears nevertheless that it can be used as a food additive, in particular in fibers (C) and/or yogurts (D), because in this case the protection of the SOD activity is optimized (FIG. 5).

These results demonstrate that the SOD activity contained in the active plant extract may be taken by the oral route in compositions according to the present invention which may, in addition, be mixed with some food products (such as yogurt and/or fibers) and thus protect the SOD activity. This oral delivery mode should therefore make it possible to demonstrate the functional activity of this SOD activity in the functional food.

The type of treatment followed is the following: the animals are treated with 10 SOD units/mouse each day for 2 weeks before irradiation with UV radiation.

Figure 6:
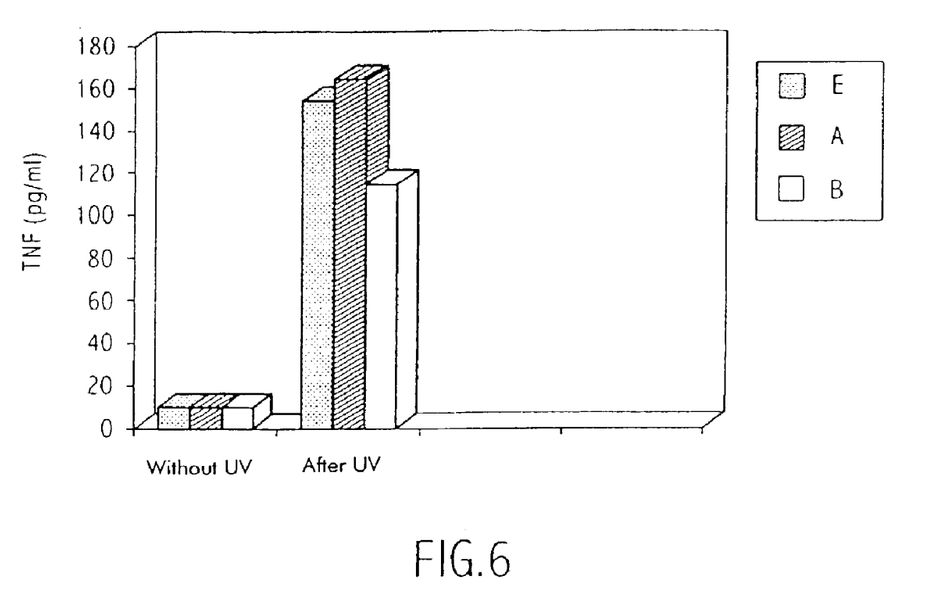
FIG. 6 represents the effect in vivo evaluated 48 hours after irradiation of the composition according to the present invention (B) taken orally by mice on inflammation induced by UV radiation compared with the uncoated active plant extract (A) and with a control (E).
Figure 7:
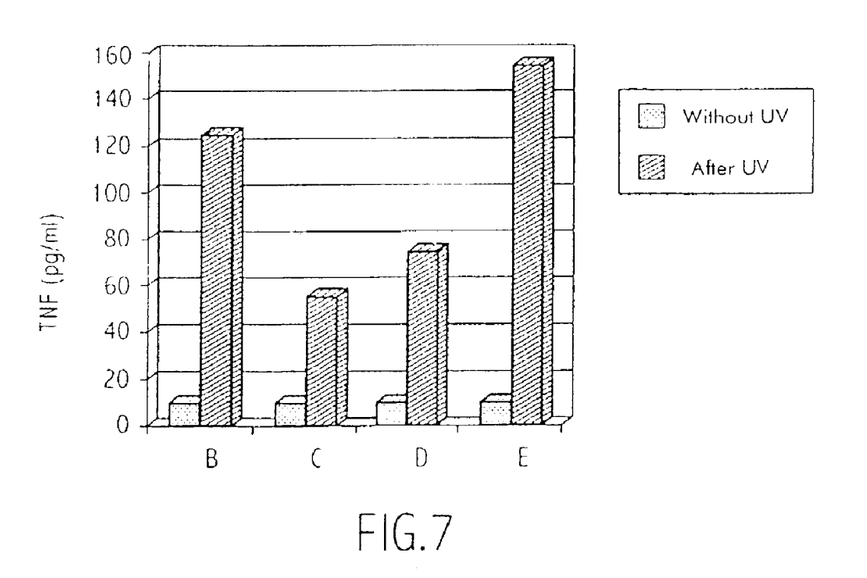
FIG. 7 represents the effect in vivo evaluated 48 hours after irradiation of the composition according to the present invention (B) taken orally on inflammation induced by UV radiation compared with the composition according to the present invention homogeneously mixed with fibers (C) or yogurt (D) and with a control (E).

In a model of human skin transplant onto "nude" mice, it is demonstrated that the oral taking of the composition according to the present invention protects against skin impairments induced by UV radiation. Thus, UV irradiation of human skin transplanted onto "nude" mice induces the production of inflammatory mediators such as TNF-α. The oral taking of the free active plant extract (EXTRAMEL®: A) has no effect whereas the taking of the composition according to Example 1 (B) has a small effect (FIG. 6). When the composition according to Example 1 is homogeneously mixed with dietary fibers (C) and/or yogurts (D), a greater protective effect may also be demonstrated (FIG. 7): 35% inhibition for the fibers/composition product according to Example 1 (C) and 25% for the yogurts/composition product according to Example 1 (D) compared with a control (E).

These preliminary results demonstrate that the taking of the composition according to the present invention complexed with other food products (fibers and yogurts) produces a protective effect in vivo against the development of a skin inflammation induced by UV radiation. These results strengthen the functional food concept by developing dietary principles which protect the dietary active agents from degradation: thus the composition according to the present invention has a maximum protective activity (although such an activity also exists for the composition according to the present invention alone by the oral route) when it is combined with other food products and therefore positions itself as a functional food additive.

EXAMPLE 3

Evaluation of the Protective Activity of the Free Active Plant Extract or in the Composition According to the Present Invention in Relation to Inflammation Associated with the Allergy Phenomenon The object of this study is to evaluate the protective effect of the active plant extract alone or protected in the composition according to the present invention, in relation to inflammation induced by allergenic substances, chemical compounds of any nature.

The inflammatory response which results from the synergy between multiple biochemical mechanisms is triggered by the release, at the level of the site attacked, of numerous proinflammatory mediators (TNF-α, NO, IL-1, IL-8, IL-6, and the like) some of which, like NO, contribute toward increasing cell death by apoptosis. The latter, a major proinflammatory mediator, appears moreover to be the main agent responsible for tissue degradations linked to the inflammatory state.

Accordingly, to evaluate the protective effect of this extract against allergic stress, we chose an experimental approach based on an in vitro model which makes it possible to determine cellular apoptosis as well as the production of proinflammatory mediators.

In this study, we chose to study, in a first instance, the production of the proinflammatory cytokines TNF-α and IL-6 and the production of the NO radical.

Materials and Methods a) Products Studied

The products used are: the composition according to Example 1 and an active plant extract of *Cucumis Melo* obtained from the company BIONOV (EXTRAMEL®). This is therefore the free extract and the extract protected by coating with a fat-soluble agent according to the present invention.

b) Course of the Study

Cells

The keratinocytes are obtained from primary cultures of foreskins and are allowed to proliferate in a conditioned medium (KGM medium) for two weeks before use. At confluence, the pure keratinocytes are cultured in 24-well plates at $10^6$ cells/ml in a growth medium in the presence or in the absence of the product to be tested for 24 h, and are then stimulated.

Medium for Evaluating the Effects of the Products Studied

During the evaluation of the product, the cells are cultured in Iscove medium supplemented with antibiotics (100 SOD units/ml of penicillin and 100 µg/ml of streptomycin) and fetal calf serum (5%), and they are brought into contact with the products studied at various concentrations (0.01 to 100 µg/ml) and then stimulated under the conditions presented below.

"Allergic" Stimulation

To mimic the development of an inflammatory reaction of allergic origin, the cells are preactivated with IL-4 (10 ng/ml) for 48 h so as to induce CD23 (receptor with low affinity for IgE) and then IC challenged stimulated with the IgE (IgE/anti-IgE) immune complexes. The cells thus activated are then maintained in culture for 48 h before collecting the supernatants in order to assay the mediators TNF-α, IL-6 and NO. The percentage of apoptotic cells is evaluated 72 h after stimulation.

Measurement of Apoptosis

At the end of the culture, death by apoptosis is evaluated using the Apoptag® kit, the DNA breaks being visualized by fluorescence emission. The number of cells undergoing apoptosis is therefore evaluated by counting the number of fluorescent cells out of a total of 200 cells.

Assay of the Inflammation Mediators IL-6, TNF-α and NO

The assays of the cytokines TNF-α and IL-6 are carried out on culture supernatants using ELISA assay kits, the detection thresholds being each time less than 10 pg/ml. As regards the production of NO, it is in fact the stable derivatives, i.e. the nitrites, which are measured by a calorimetric technique using the Griess reagent.

Results a) Apoptosis 72 h after activation of the cells with the IgE/anti-IgE complex, significant apoptosis is observed. The results are assembled in Table 5.

TABLE 5

Percentage of apoptotic cells after simulation of an inflammation of allergic origin

| Treatment | % apoptosis relative to the total number of cells cultured |
| --- | --- |
| Nontreated keratinocytes | 3 ± 2 |
| Keratinocytes-CD23 (treated with IL-4) | 8 ± 1 |
| Keratinocytes-CD23 + IgE IC | 45 ± 4 |

These results demonstrate that the induction of an inflammatory reaction of allergic origin induces a significant increase in death by apoptosis of the stimulated keratinocytes. This therefore makes it possible to institute this model as a model for the evaluation of product having a "protective" activity profile.

b) Antiapoptotic Effect of the Active Plant Extract Alone Extramel(: Influence of the Addition Conditions To determine the capacity of the active plant extract alone EXTRAMEL® to modulate apoptosis induced by an allergic stress, preventively, immediately or following stress, this extract was added 24 h before stimulation, at the time of stimulation and finally 24 h after, respectively.

The active plant extract alone EXTRAMEL® is introduced at 10 μg/ml. This experiment was carried out in triplicate. The results are assembled in Table 6.

TABLE 6

Percentage of apoptotic cells in the "allergic inflammation" model

| IgE IC | Experiment 1 | Experiment 2 | Experiment 3 | Mean |
| --- | --- | --- | --- | --- |
| Without active plant extract EXTRAMEL® | 30 | 25 | 38 | 31 |
| Active plant extract alone | 11 | 15 | 21 | 15.6 |

TABLE 6-continued

Percentage of apoptotic cells in the "allergic inflammation" model

| IgE IC | Experiment 1 | Experiment 2 | Experiment 3 | Mean |
| --- | --- | --- | --- | --- |
| EXTRAMEL® (T − 24 h) Active plant extract alone | 32 | 20 | 26 | 26 |
| EXTRAMEL® (T0) Active plant extract alone | 33 | 27 | 35 | 31.6 |
| EXTRAMEL® (T + 24 h) | | | | |

Under the conditions of the experiment, a marked reduction in apoptosis is observed when the active plant extract alone EXTRAMEL® is added 24 h before irradiation. The active plant extract alone EXTRAMEL® therefore exerts a protective activity.

c) Production of Cytokines and of NO

The capacity of the active plant extract alone EXTRAMEL® to modulate the production of proinflammatory mediators by sensitized keratinocytes was evaluated according to the following experimental conditions: introduction of the active plant extract alone EXTRAMEL® 24 h before stimulation, or just before stimulation, or 24 h after irradiation.

The active plant extract alone EXTRAMEL® is introduced at 10 μg/ml. Each experiment was carried out in triplicate. The results are assembled in Table 7.

TABLE 7

Assay of the mediators 48 h after allergic stimulation

| Treatment | TNF (pg/ml) | IL-6 (pg/ml) | $NO_2^-$ (μM) |
| --- | --- | --- | --- |
| None or active plant extract alone EXTRAMEL® | Not detectable in the 3 experiments | Not detectable in the 3 experiments | Mean: 1.00 |
| IgE IC | Mean: 632 | Mean: 428 | Mean: 17.3 |
| IgB IC Active plant extract alone EXTRAMEL® (T − 24 h) | Mean: 152 | Mean: 208 | Mean: 3.6 |
| IgE IC Active plant extract alone EXTRAMEL® (T0) | Mean: 620 | Mean: 525 | Mean: 9 |
| IgE IC Active plant extract alone EXTRAMEL® (T + 24 h) | Mean: 655 | Mean: 502 | Mean 10.1 |

The allergic stress, under the conditions used for these experiments, stimulates the production of the cytokines TNF-α and IL-6 and the production of NO, via the activation of inducible NO-Synthase in these cells.

Moreover, a reduction in the production of the proinflammatory cytokines and of the nitro derivatives is observed when the active plant extract alone EXTRAMEL® (10 μg/ml) is added preventively (T−24 h) whereas the addition immediately (T0) or 24 h after the stimulations (T+24 h) has much less effect on the production of these mediators.

d) Comparison of the Effect of the Active Plant Extract Alone Extramel® with the Composition According To Example 1

The composition according to Example 1 was tested under the experimental conditions described above and, in the same quantity, exhibits better efficacy than the active plant extracts alone EXTRAMEL®. The results are assembled in Table 8.

TABLE 8

Comparison of the effect of the active plant extract alone EXTRAMEL ® and the composition according to Example 1

| Treatment | Toxicity % mortality | TNF (pg/ml) | $NO_2^-$ (μM) |
|---|---|---|---|
| None Active plant | 5 | Not detectable | Mean: 0.8 |
| extract alone EXTRAMEL ® | 5 | Not detectable | Mean: 1.00 |
| Composition according to Example 1 | 5 | Mean: 50 | Mean: 1.0 |
| IgE IC | 35 | Mean: 508 | Mean: 19.3 |
| IgE IC Active plant extract alone EXTRAMEL ® | 20 | Mean: 168 | Mean: 5.6 |
| IgE IC Composition according to Example 1 | 10 | Mean: 62 | Mean: 0.8 |

CONCLUSION

It appears clearly in this study that the active plant extract alone EXTRAMEL® exerts a protective effect against the inflammatory phenomenon linked to an allergic response and that the compositions according to the invention, that is to say this extract protected by a coating with the aid of a fat-soluble agent according to the invention, are more effective than the active plant extract alone.

The composition according to the invention significantly reduces cellular apoptosis induced by allergic stress.

This effect appears to be linked to the regulation of the inflammatory phenomenon linked to the allergy since the composition according to the invention significantly reduces the production of TNF-α, of IL-6 and of NO by the sensitized keratinocytes.

An active agent capable of reducing inflammation linked to the allergy phenomenon, the composition according to the invention protects the skin tissue from inflammation caused by allergenic compounds, chemical substances of any nature (metals such as nickel, protein substances, cosmetic excipients, and the like) present in products for daily use as well as in environmental pollutants.

EXAMPLE 4

Evaluation of the Protective Activity of the Cream According to Example 2 Against UV Radiation The evaluation model is performed on a normal skin explant irradiated or otherwise with UV radiation (A+B).

The production of TNF was chosen as inflammation marker.

The product tested is the semisolid preparation for local application according to Example 2, that is to say containing a composition according to Example 1.

The doses tested on the skin before exposure to UV radiation are:

SOD1: 1 mg/cm² of skin,
SOD2: 0.5 mg/cm² of skin,
SOD3: 0.1 mg/cm² of skin and
SOD4: 0.05 mg/cm² of skin.

The TNFs are measured after exposure to UV radiation with the aid of an ELISA assay kit.

Figure 8:
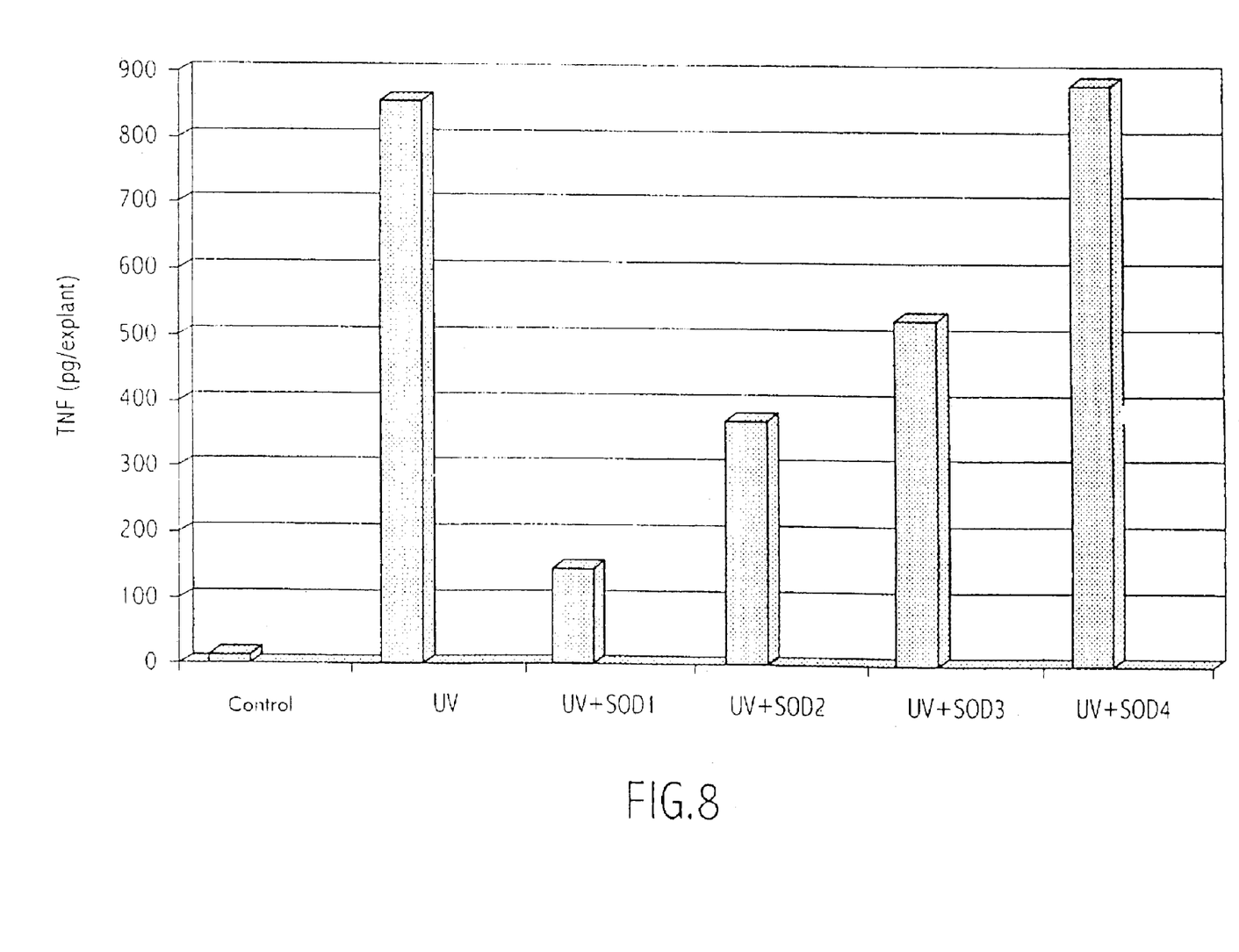
FIG. 8 represents the effect of the semisolid preparation for local application containing a composition according to the present invention on inflammation induced by UV radiation according to the dose of cream applied and compared with a control.

The results (FIG. 8) demonstrate a protective skin activity of the composition according to the present invention formulated for topical application against inflammation induced by UV irradiation, in particular at doses greater than 0.05 mg/cm² of skin.

The invention claimed is:

1. A method for coating and/or microencapsulating with a hydrogenated palm oil a *Cucumis melo* extract in the form of a powder whereby the *Cucumis melo* extract contains superoxide dismutase, comprising the following steps:
    a) melting the hydrogenated palm oil;
    b) spraying the melted hydrogenated palm oil onto a fluidized bed of the *Cucumis melo* extract powder, wherein the fluidized bed is at a temperature of about 40° C.

2. The method according to claim 1, wherein the fluidized bed of step b) is at a low moisture content.

3. The method according to claim 1, wherein the *Cucumis melo* is a progeny of the cell line 95LS444 or of one of the hybrid lines derived from 95LS444.

4. The method according to claim 1, wherein the *Cucumis melo* extract content of the coated extract obtained in step b) is between 20 and 50% by weight relative to the total weight of the coated extract.

5. A method for preparing a cosmetic, pharmaceutical or food composition wherein the method comprises the step of mixing the coated extract obtained in step b) of the process according to claim 1, with yogurt and/or fibers.

6. The method according to claim 5, wherein the mixing is an homogenous mixing.

7. The method according to claim 1, wherein the *Cucumis melo* extract is in the form of a freeze-dried powder.

* * * * *